United States Patent
Armant et al.

(10) Patent No.: US 10,344,315 B2
(45) Date of Patent: Jul. 9, 2019

(54) IDENTIFICATION AND ANALYSIS OF FETAL TROPHOBLAST CELLS IN CERVICAL MUCUS FOR PRENATAL DIAGNOSIS

(71) Applicant: Wayne State University, Detroit, MI (US)

(72) Inventors: D. Randall Armant, Saint Clair Shores, MI (US); Michael P. Diamond, Grosse Pointe Shores, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 14/436,270

(22) PCT Filed: Oct. 18, 2013

(86) PCT No.: PCT/US2013/065570
§ 371 (c)(1),
(2) Date: Apr. 16, 2015

(87) PCT Pub. No.: WO2014/062995
PCT Pub. Date: Apr. 24, 2014

(65) Prior Publication Data
US 2015/0267240 A1 Sep. 24, 2015

Related U.S. Application Data

(60) Provisional application No. 61/715,854, filed on Oct. 19, 2012.

(51) Int. Cl.
| | | |
|---|---|---|
| *C12Q 1/24* | (2006.01) | |
| *C12Q 1/6888* | (2018.01) | |
| *G01N 33/569* | (2006.01) | |
| *C12N 5/073* | (2010.01) | |

(52) U.S. Cl.
CPC .............. *C12Q 1/24* (2013.01); *C12N 5/0605* (2013.01); *C12Q 1/6888* (2013.01); *G01N 33/56966* (2013.01); *C12N 2503/00* (2013.01); *C12Q 2600/156* (2013.01); *G01N 2333/70539* (2013.01); *G01N 2800/368* (2013.01)

(58) Field of Classification Search
None
See application file for complete search history.

(56) References Cited

U.S. PATENT DOCUMENTS

| | | | |
|---|---|---|---|
| 5,447,864 A | 9/1995 | Raybuck et al. | |
| 5,858,649 A | 1/1999 | Asgari et al. | |
| 2002/0009759 A1* | 1/2002 | Terstappen | B03C 1/01 435/7.23 |
| 2004/0197832 A1 | 10/2004 | Amiel et al. | |
| 2005/0123914 A1 | 6/2005 | Katz et al. | |
| 2005/0181429 A1 | 8/2005 | Fejgin et al. | |
| 2007/0224597 A1 | 9/2007 | Pircher et al. | |
| 2008/0261822 A1 | 10/2008 | Fejgin et al. | |
| 2009/0286271 A1 | 11/2009 | Karumanchi et al. | |
| 2011/0027795 A1* | 2/2011 | Mantzaris | C12N 5/0603 435/6.12 |
| 2011/0183338 A1 | 7/2011 | Bischoff | |
| 2012/0149014 A1 | 6/2012 | Allman et al. | |
| 2013/0171672 A1 | 7/2013 | Hussa et al. | |
| 2015/0267240 A1 | 9/2015 | Armant et al. | |

OTHER PUBLICATIONS

Sigma-Aldrich, Product information for N-Acetyl_L-cysteine, available via url: <sigmaaldrich.com/catalog/product/mm/112422?lang=en&region=US>, printed on Aug. 1, 2017.*
Bolnick et al Fertility and Sterility. Published online Sep. 2012. 98(3): p. S133, Abstract P-72.*
Grutzkau et al Cytometry. May 2010. 77A:643-647.*
Bajpayee, S., Prenatal Genetic Diagnosis Using Transcervically Derived and Immunomagnetically Isolated Trophoblast Cells, Wayne State University Honors College Theses, Dec. 13, 2012.
Bolnick, J. et al., Trophoblast retrieval and isolation from the cervix (TRIC) for noninvasive prenatal screening at 5 to 20 weeks of gestation, *Fertility and Sterility*, 102(1): 135-142, Jul. 2014.
Bolnick, A. et al., Trophoblast Retrieval and Isolation from the Cervix for Noninvasive, First Trimester, Fetal Gender Determination in a Carrier of Congenital Adrenal Hyperplasia, Reproductive Sciences, pp. 1-6, Feb. 25, 2016.
Bolnick, J. et al., Altered Biomarkers in Trophoblast Cells Obtained Noninvasively Prior to Clinical Manifestation of Perinatal Disease, Manuscript, Mar. 2016.
Fritz, R. et al., Noninvasive detection of trophoblast protein signatures linked to early pregnancy loss using trophoblast retrieval and isolation from the cervix (TRIC), Fertility and Sterility, 104(2): 339, Aug. 2015.
Fritz, R. et al., Trophoblast retrieval and isolation from the cervix (TRIC) is unaffected by early gestational age or maternal obesity, *Prenatal Diagnosis*, 35: 1218-22, 2015.
Huang, Y. et al., Acquisition of fetal cells from transcervical cells in early pregnancy and immunocytochemical study, Dept. of Obstetrics and Gynecology, Nanfang Hospital, Southern Medical University, Guangahou, China (Abstract).

(Continued)

*Primary Examiner* — Carla J Myers
(74) *Attorney, Agent, or Firm* — Dinsmore & Shohl LLP

(57) ABSTRACT

A method of retrieving fetal cells from an endocervical sample by removing the mucus from the endocervical sample by disassociating fetal cells and maternal cells in the endocervical sample; and isolating disassociated fetal cells from other cells in the endocervical sample. Also provided is a method of retrieving fetal cells from an endocervical sample, by obtaining a mixture of disassociated cells prepared by the above method, treating the cells with a fetal-specific antibody, identifying cells that have bound to the fetal-specific antibody, and isolating the identified cells. The disassociated cell prepared by the above method can be analyzed and used for a variety of purposes including, but not limited to, the identification of fetal cells among cervical cells, determination of fetal cell density to predict high risk pregnancy, genetic analysis of fetal cells, and determination of growth factor or other biomarker expression to predict obstetrical disorders.

11 Claims, 1 Drawing Sheet

(56) References Cited

OTHER PUBLICATIONS

Imudia, A. et al., Retrieval of trophoblast cells from the cervical canal for prediction of abnormal pregnancy: a pilot study, Human Reproduction, 24(9): 2086-92, Jun. 4, 2009.
Imudia, A. et al., Transcervical Retrieval of Fetal Cells in the Practice of Modern Medicine: A Review of the Current Literature and Future Direction, Fertil Steril, 93(6): 1725-30, Apr. 2010.
Katz-Jaffe, M. et al., DNA identification of fetal cells isolated from cervical mucus: potential for early non-invasive prenatal diagnosis, BJOG: An International Journal of Obstetrics and Gynecology, 112: 595-600, May 2005.
Evers, D. et al., The effect of formaldehyde fixation on RNA: optimization of formaldehyde adduct removal, The Journal of Molecular Diagnostics, 13(3): 282-288, May 1, 2011.
Wong, H., Isolation of human leukocyte antigen G/cytokeratin 7 positive fetal cells from transcervical samples for potential use in prenatal genetic diagnosis, a thesis submitted in partial fulfillment of the requirements for the Degree of Master of Philosophy at The University of Hong Kong, Jan. 2015.

\* cited by examiner

IDENTIFICATION AND ANALYSIS OF FETAL TROPHOBLAST CELLS IN CERVICAL MUCUS FOR PRENATAL DIAGNOSIS

GOVERNMENT SUPPORT

This invention was made with government support under R21 HD071408 awarded by National Institutes of Health. The government has certain rights in the invention.

BACKGROUND OF THE INVENTION

1. Field of the Invention

The present invention relates to cell isolation. More specifically, the present invention relates to non-invasive methods of cell retrieval and isolation.

2. Description of the Related Art

It is thought that due to changing demographics, increased exposure to environmental toxins and intervention in the reproductive process, developmental abnormalities may be on the rise. The risk to any pregnant couple of having a live born infant with a chromosomal abnormality or structural defect has been previously estimated to be between 3% and 5%. Because of this considerable risk, much effort has been expended in recent decades to identify pregnancies at risk of chromosomal anomalies and genetic disorders at an early gestational age. The current standard of care involves screening maternal analytes and ultrasound markers, each alone or in combination, to identify at risk pregnancies, followed by referral for definitive diagnostic tests that include amniocentesis and chorionic villous sampling. While the former screening modalities have considerable rates of false positives and false negatives, the latter diagnostic tests are invasive and carry significant risk of fetal loss. Indeed, Mujezinovic et al. conducted a systematic analysis of 45 studies and reported a fetal loss rate of 1.9% for amniocentesis and 2% for chorionic villous sampling. Therefore, the search to develop safer methods to obtain genetic material from the fetus is ongoing and desperately needed.

Another alternative for prenatal diagnosis is preimplantation genetic diagnosis (PGD), which involves screening for chromosome abnormalities or single gene disorders in an embryo prior to implantation. The main advantage is avoidance of elective pregnancy termination, while offering a high likelihood that the fetus will be free of a specific disorder. Although PGD is an attractive method for prenatal diagnosis, it is an adjunct of assisted reproductive technology that requires in vitro fertilization, which has its own risks and high costs. Thus, PGD is not feasible as a universal diagnostic tool for genetic abnormalities in the general population.

Identification of fetal cells in maternal serum has been attempted, but this approach has been hindered by the relative rarity of fetal cells in maternal blood (1 fetal cell per $10^6$-$10^7$ maternal cells) and associated difficulties in their isolation and analysis. Overall, the projected clinical efficacy has been disappointing. Nevertheless, recent discovery of fetal nucleic acids in maternal plasma has introduced several new possibilities for noninvasive prenatal screening of chromosomal aneuploidies. Anomalies are revealed after the first ten weeks of gestation by measuring the allelic ratio of single nucleotide polymorphisms in the coding region of the human genome, analysis of DNA fragments with different patterns of DNA methylation between fetal and maternal DNA, enrichment of the fractional concentration of fetal DNA in maternal plasma using physical or chemical methods, and the development of more precise digital polymerase chain reaction (PCR)-based methods for fetal nucleic acid analysis. Specific inheritable diseases could also be diagnosed with fetal DNA, but due to the fragmented nature of circulating cell-free fetal DNA, maternal plasma screening is not considered a reliable approach.

Prior to 13-15 weeks of gestation, it is believed that small areas of erosions allow trophoblast cells to cross the decidua capsularis and reach the uterine cavity. This process becomes less likely after the amniochorionic membrane seals the uterine cavity and the internal cervical os, which is thought to occur at three months of gestation. In 1971, Shettles suggested that during early pregnancy, a similar shedding occurs into the uterine cavity, making chorionic cellular elements from the degenerating villi available in the endocervical canal. The possibility of capturing fetal cells from accessible regions of the reproductive tract suggests new approaches for early prenatal diagnosis. The isolation of fetal cells from the cervix and the endometrial cavity offers an attractive non-invasive alternative for very early (6-14 weeks, possibly as early as 5 weeks) diagnosis. Since its first description, several investigators have reported the feasibility of isolating fetal cells from the cervical mucus or from fluid obtained by lavage of the endometrial cavity with varying degrees of success. The existing literature suggests that the present status of transcervical cell (TCC) sampling in prenatal diagnosis is experimental, but carries excellent potential for both genetic diagnosis and prediction of pregnancy outcome as laboratory methods are refined and standardized.

The ideal method that would reliably yield fetal cells in appreciable quantity should have no negative impact on the ongoing pregnancy and be free from infectious or traumatic complications. It should also be simple to perform and cost effective, with minimal inter-observer variability. A number of techniques have been devised to retrieve TCC samples from the endocervical canal and the endometrial cavity, including smears obtained with cotton swabs or a cytobrush, aspiration of cervical mucus with a catheter, endometrial biopsy with a Pipelle, and lavage of the endocervical canal or the uterine cavity, all with variable levels of success.

At present, the existing literature differs vastly and is often contradictory in projecting the relative efficacy of the currently available methods for retrieving fetal cells. Previously, emphasis has been placed on the feasibility of obtaining fetal cells and establishing their diagnostic utility, rather than a direct comparison of the relative efficacy of the various methods in randomized control trials, as recently reported. It has been noted that the post-collection processing of the TCC samples has tremendous variation from one study to another, which directly affects the yield of useful information. Techniques used to identify the fetal cells and the diagnostic end points (fetal sex vs gene disorders) have also differed, yielding heterogeneous groups for comparison with non-uniform results. Thus, there is a lack of information on well-described techniques for sample collection and analysis, resulting in considerable dependence on the technique and skill of individual operators.

For example, in the landmark 1971 report by Shettles, identification of the Y chromosome was used to determine fetal sex from midcervical mucus samples obtained with cotton swabs. A limitation of using cotton swabs to retrieve TCC samples is the entrapment of cells within the cotton, which may reduce yield. The use of a cytobrush for cervical mucus retrieval or lavage of the endocervical canal with normal saline offers viable alternatives for TCC collection.

A cytobrush inserted through the external os to a maximum depth of 2 cm and rotated at least a full turn during removal provides fetal cells in diagnostic quantities. However, other investigators failed to reproduce this success. Aspiration of the endocervical mucus with a single cannula also results in the detection of fetal cells in up to 70% of TCC samples from mothers with male fetuses. Furthermore, Kingdom et al. demonstrated that lavage of the endocervical canal retrieves more trophoblast cells than the cytobrush, and that cytobrush specimens may have a higher incidence of debris and maternal endocervical cells. A more effective method in terms of fetal cell yield is intrauterine lavage (IUL), in which a flexible catheter connected to a syringe filled with normal saline is used to flush the endometrial cavity. IUL and the other methods for TCC sampling are illustrated in an article by Adinolfi and Sherlock.

Human leukocyte antigen (HLA)-G is a class Ib major histocompatability complex protein that is expressed by human extravillous cytotrophoblast cells and is absent in all other uterine and placental cell populations. In 2003, Bulmer et al. employed MAbs against HLA-G to identify cytotrophoblasts cells in TCC samples retrieved by IUL. Cytotrophoblast cells characterized by their large, irregular hyperchromatic nuclei were HLA-G positive and were identified in 12 of 23 (52%) TCC samples. Interestingly, molecular examination of DNA by QF-PCR in HLA-G positive elements collected by laser capture micro-dissection from four of the patients revealed fetal markers, demonstrating the utility of this approach for prenatal genetic diagnosis. The combined immunohistochemical and molecular approach used in this study revealed considerable variation between the samples. The sensitivity of MAb labeling was relatively low even though HLA-G reactivity provides high specificity for identification of fetal-derived trophoblast cells. HLA-G is expressed by extravillous cytotrophoblast cellular elements, but not by syncytial fragments, limiting its ability to identify all fetal cells. The necessity for a set of MAbs reacting exclusively against antigens expressed on specific subpopulations of trophoblast cells will be crucial for an immunohistochemical approach to identify fetal cells comprehensively. More recently, it was demonstrated that extravillous cytotrophoblast cells could be consistently (>95% of specimens) identified using HLA-G as an antigenic marker in TCC specimens collected by cytobrush into a fixative rinse and prepared on microscope slides free of interfering mucus. Slides stained with the same antibody against HLA-G used by Bulmer et al. and counterstained with hematoxylin reveal a small number of antibody-labeled cytotrophoblast cells on a dense background of cervical cell nuclei. Trophoblast frequency was approximately one in two thousand for all pregnancies successfully sampled between gestation weeks six and fourteen, while this value was reduced four to five-fold in specimens retrieved from women with ectopic pregnancy or blighted ovum. These findings suggest that, in addition to genetic testing, information can be gleaned from TCC analysis alerting clinicians to at-risk pregnancies.

The recovery and analysis of fetal cells shed from the placenta into the cervical canal could provide wider availability of prenatal genetic diagnostics to the general patient population. With improvements in the efficacy and safety of trophoblast collection by TCC sampling using the cytobrush, and in the identification and isolation of those cells expressing trophoblast markers, small quantities of fetal DNA could be readily obtained for genetic testing. New sensitive technologies, such as those now under development for analysis of fetal DNA in maternal serum, could yield extensive information about the fetal genome from modest numbers of isolated cells. The ability to procure cytotrophoblast cells by TCC as early as six weeks of gestation could make this vital information available much earlier than current technologies, including the analysis of fetal DNA in maternal serum. It would therefore be useful to develop a non-invasive method for isolated trophoblasts.

SUMMARY OF THE INVENTION

According to the present invention there is provided a method of retrieving fetal cells from an endocervical sample by removing the mucus from the endocervical sample by disassociating fetal cells and maternal cells in the endocervical sample; and isolating disassociated fetal cells from other cells in the endocervical sample. Also provided is a method of retrieving fetal cells from an endocervical sample, by obtaining a mixture of disassociated cells prepared by the above method, treating the cells with a fetal-specific antibody, identifying cells that have bound to the fetal-specific antibody, and isolating the identified cells.

The disassociated cell prepared by the above method can be analyzed and used for a variety of purposes including, but not limited to, the identification of fetal cells among cervical cells, determination of fetal cell density to predict high risk pregnancy, genetic analysis of fetal cells, and determination of growth factor or other biomarker expression to predict obstetrical disorders, including preeclampsia.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENTS

Figures 1, 2:
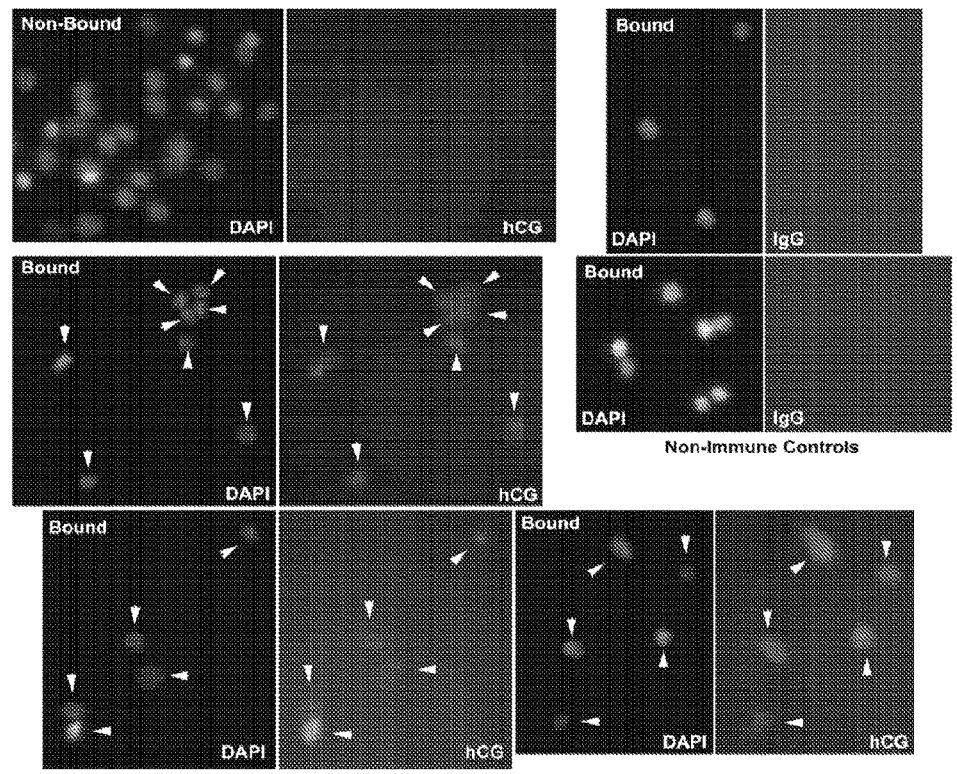
FIG. 1 show cells isolated from TCS that express β-hCG. Each field was imaged to show the fluorescence of DAPI nuclear stain (left) or secondary antibody (right). The cells in the Bound fraction were all labeled by anti β-hCG, indicated by the arrowheads in matched DAPI and hCG images, while none of the Non-bound cells were labeled. Bound cells labeled with non-immune IgG were also not fluorescent, indicating a low non-specific binding.
FIG. 2 shows sex determination with isolated trophoblast cells. PCR analysis of genes on the X (DMD) and Y (SRY) chromosomes using isolated DNA from foreskin fibroblast (Fb) cells, individual fixed Fb cells or ten individual isolated trophoblast cells, as indicated, using primers for just SRY, just DMD or both genes in a multiplex assay. The fetus of the patient in the upper gel appears to be male, while the lower gel shows a female fetus. Some of the reactions in the lower sample appeared to fail, most likely due to loss of the cell during transfer into the PCR tube.

The present invention provides a method for obtaining and using fetal material obtained en masse during the first trimester of pregnancy from the cervix or uterine cavity to perform prenatal diagnosis. The method includes disassociating the fetal cells and maternal cells from the mucus of a sample and isolating the disassociated fetal cells from other cells in an endocervical sample. Additionally, the methods of the present invention enable non-invasive acquisition of EVT cells and permits comparison of protein expression levels with pregnancy outcomes. These findings identified a robust panel of EVT biomarkers that could inform during the first and second trimester about patient risk for PE or IUGR or other obstetrical disorders. The methods of the present invention can be used as a clinical laboratory service. The method includes the steps of collecting cells, placing the collected cells in a fixative solution, removing the mucus by acidification, washing the remaining cells by centrifugation, and preparing the cells on microscope slides.

The specimens can be obtained using standard non-invasive methods known to those of skill in the art. Examples include, but are not limited to, intrauterine lavage, aspiration of cervical mucus, or removal of surface tissue from the cervical as or endocervical canal. The preferred method is to collect mucus from the endocervical canal using a cytological brush inserted about 2 cm past the external os and rotating to remove and capture the mucus plug, while minimally abrading the cervical tissue. The cytological brush is then rinsed into a fixative solution composed of low pH (4-6) buffer and an alcohol. For example, a standard 3% acetic acid, 7% sodium acetate, 50% methanol mixture can be used. Clinicians can be instructed to collect specimens using the ThinPrep® kit from women found to be pregnant and still in the first or second trimester. This kit contains a cytological brush and includes 20 ml of fixative solution.

The collected cells are isolated from the mucus by acidification. Acidification can be accomplished using methods known to those of skill in the art. For example addition of a 3% solution of acetic acid to reduce the pH of the fixative containing cells to 2 to 4, corresponding to a dilution of the acetic acid solution by 10 to 20 fold in the fixative.

Once the specimen has been obtained, fetal cells, or other cell types of clinical importance, such as immunological cell subtypes, can be isolated and identified in collected samples. This can be accomplished using methods known to those of skill in the art including, but not limited to, using evidence for the presence of the male Y chromosome, comparison of allelic profile with maternal allelic profile and expression of trophoblast marker molecules (e.g., cytokeratin7, hCG, HLA-G, placental alkaline phosphatase, hyaluronic acid targeted by monoclonal antibody NDOG1, and the unknown target of monoclonal antibody FT141.1, a.k.a. FT1.41.1). In most cases, the analysis of fetal cells would involve genetic diagnosis by fluorescent in situ hybridization (FISH) or the polymerase chain reaction (PCR). The methods can be used to predict pregnancy outcome based on tests performed on the cells collected using the ThinPrep® kit.

The major disadvantages of sampling fetal cells deposited in the cervical mucus plug are that there are many more maternal cells present than fetal cells and that mucus interferes with many tests due to aggregation of cells and background fluorescence of the mucus. The first problem will be addressed using robust fluorescent markers for trophoblast cells. A limitation of HLA-G as a marker is that it does not recognize all trophoblast subpopulations (e.g., syncytial trophoblast fragments). Cytokeratin is expressed by all trophoblast subpopulations, but it may also be found in some maternal cell types, leading to false positives. The problem of mucus has been solved by acidification to dissolve it. The number of trophoblast cells present in the samples, which could vary, may limit the method. If the number is too low, flow cytometry would become impractical. However, immunofluorescence microscopy would be a viable approach as long as several HLA-G-positive cells can be located in a microscopic field prepared from up to 1 ml of sample.

The recovery and analysis of fetal cells shed from the placenta into the cervical canal provides wider availability of prenatal genetic diagnostics to the general patient population. With improvements in the efficacy and safety of trophoblast collection by TCC sampling using the cytobrush, and in the identification and isolation of those cells expressing trophoblast markers, small quantities of fetal DNA could be readily obtained for genetic testing. New sensitive technologies, such as those now under development for analysis of fetal DNA in maternal serum, could yield extensive information about the fetal genome from modest numbers of isolated cells. The ability to procure cytotrophoblast cells by TCC as early as six weeks of gestation could make this vital information available much earlier than current technologies, including the analysis of fetal DNA in maternal serum. Over the next few years, more studies using TCC sampling for prenatal diagnosis of chromosome abnormalities, paternity testing, screening for abnormal pregnancies in the first trimester and early diagnosis of obstetrical problems are expected, all of which could be performed using the cells isolated from the methods described herein.

Additionally, ectopic pregnancy complicates about 1-2% of all pregnancies and occurs when the developing blastocyst implants at a site other than the fundus of the uterine cavity, most commonly in the fallopian tube. Delayed clinical diagnosis of this abnormality can result in a dismal maternal outcome. The presence of fetal trophoblast cells in the cervical canal during the first trimester provides a non-invasive approach for predicting abnormal pregnancy through transcervical sampling.

In the present embodiment, a commercially available kit (ThinPrep®, Hologic Corporation, Marlborough, Mass.) is used to collect cells during the first trimester of pregnancy from the cervix. This is minimally invasiveness, as PAP smear tests are routinely recommended during pregnancy. Using the ThinPrep® kit, a provided cytobrush is used to collect mucus and cellular material from the cervix between the inner os and outer os, as directed by the manufacturer. The collected cells are rinsed into PreservCyt® transport medium supplied by the manufacturer in a vial. PreservCyt® transport medium contains a methanol-acetic acid-based fixative. Samples are stored at room temperature or under refrigeration until analysis.

A slide preparation can be made by first acidifying the specimen to dissolve mucus and free trapped cells for immunohistochemical staining. The specimen is then placed into a Shandon EZ mega funnel affixed to a microscope slide and centrifuged in a Cytospin3 centrifuge. This procedure yields evenly spread cells within a delineated area on the slide and free of interfering mucus. Alternatively, an automated processor for preparation of cytological slides could be used. One example is the ThinPrep2000 (Hologic)

The cells are then stained with antibody against HLA-G, a major histocompatibility protein expressed only by fetal trophoblast cells. Other trophoblast markers can be used, for example the β subunit of chorionic gonadotropin (β-CG), or placental lactogen (PL), among others, but some (e.g., cytokeratin 7) are less specific. Immunofluorescence microscopy or flow cytometry is used to identify the fluorescently-labeled trophoblast cells. A protein of interest can be queried in the HLA-G-positive cells using an appropriate antibody and a secondary antibody with a different fluorescent label (double labeling). Alternatively, a FISH procedure could be used for genetic analysis of the HLA-G positive cells, for example it could be used to detect chromosome number or a particular gene sequence if there were a way to identify the fetal cells, such as the presence of the Y chromosome. A different strategy would be necessary for a female fetus, however. It has been demonstrated (Imudia et al., 2009) that it is possible to use an enzyme-linked secondary antibody for HLA-G identification that can be visualized by bright field microscopy (e.g., with diaminobenzidine substrate for a peroxidase tag), and the cells of interest could be isolated by laser capture microdissection for genetic analysis by PCR.

It has been found that placentas from women with the hypertensive disorder pre-eclampsia have altered expression of several proteins (epidermal growth factor [EGF], transforming growth factor-a [TGFA], heparin-binding EGF-like growth factor [HBEGF]). The fluorescent double labeling method therefore can be used to screen the expression of these proteins in trophoblasts isolated from cervical collections during the first trimester, months before any clinical symptoms present. Therefore, this method could provide a diagnostic tool to identify women at risk for developing pre-eclampsia later during their pregnancy.

Currently, chorionic villous sampling (CVS) or amniocentesis can be used for prenatal diagnosis of fetal chromosomal abnormality. Both methods are invasive and associated with potential pregnancy loss. CVS can only be performed after 10 weeks, and amniocentesis has to be done after 14 weeks gestation. It is much less desirable to perform termination of pregnancy after the second trimester begins. The methods of the present invention allow the test to be performed in early first trimester and in a non-invasive manner.

In another embodiment, the methods can be used to test the expression of biomarkers that are indicative of obstetrical disorders. The biomarkers can include growth hormones, proteins, and RNA. By way of example, the methods can be used to test the expression of proteins by double-labeling cells with fluorescent antibodies to determine if EGF, TGFA or HBEGF are reduced in trophoblast cells. These changes have been observed in the trophoblast cells of placentas delivered from women with pre-eclampsia. Since 5% of all pregnant women eventually develop pre-eclampsia, this would be a beneficial test to perform routinely at the time of a positive pregnancy test. Those women found to be at risk for the disorder, could be instructed to take precautions against developing hypertension long before clinical symptoms first appear.

In another embodiment, the method can include conducting genetic analysis of transcervical trophoblast cells. Trophoblast DNA can be obtained (1) by laser capture microscopy of anti-HLA-G labeled cells (or using other antibodies that distinguish trophoblast cells from resident maternal cells of the cervix), or (2) with anti-HLA-G affinity magnetic beads/nanoparticles to isolate trophoblast cells. Genetic, immunological or other biochemical analyses can then be performed by a variety of whole-cell approaches. For example, PCR with or without reverse transcription, immunohistochemistry, whole genome amplification (WGA) followed by comparative genomic hybridization or sequencing, metabolite assays, small compound assays and other tests would be adaptable. Alternatively, fetal and maternal DNA can be assessed in unfractionated transcervical samples using a digital PCR approach.

The genetic analysis can include, for example, FISH, sequencing or PCR based methods. Alternatively, magnetic beads can also be used prior to immunofluorescence as a way to enrich for the cells of interest and streamline analysis. Dynal Magnetic beads are available from Invitrogen (Carlsbad, Calif.) with secondary antibodies attached or chemical coupling groups that can be used to attach anti-HLA-G. They are mixed with the cells after acidification and neutralization and decorate target cells (trophoblast). Holding a magnet against the test tube or inserting the tube into a device like the DynaMag™-Spin magnet (Life Technologies) for 5 minutes, the suspended cells are aspirated off, leaving behind the magnet-bound cells coated with beads. After three washes, it is possible to enrich about 1,000 to 10,000 fold, which should be adequate to isolate most of the trophoblast cells. The cells can be examined microscopically to verify the presence of beads and manually remove any cells without beads that contaminate the sample. Then, additional testing can be conducted as disclosed in more detail herein.

In another embodiment, the fetal trophoblast cells can be isolated from the resident maternal cells after their collection so they can be used in genetic or biochemical tests. The specificity of the anti-HLA-G antibody is used for this purpose by coupling it to magnetic nanoparticles for trophoblast isolation. For example, the method can use 10 µl of 250 nm nanoparticles conjugated to anti-mouse IgG or Protein A (Clemente Associates, Madison, Conn.) and incubated with 5 µg of mouse monoclonal anti-HLA-G antibody (Clone: 4H84, BD Biosciences, San Diego, Calif.; or clone G233; Exbio, Prague) overnight on a rotary shaker at 4° C. The particles are separated from unbound antibody by placing tubes in a DynaMag™-Spin magnet (Life Technologies) for 5 minutes and then removing the liquid while the magnetic nanoparticles are retained. Cells collected from a transcervical specimen are then added to the nanoparticles and incubated at room temperature for one to 24 hours on a rotary shaker at 4° C. The sample is magnetized and unbound cells are removed. After three washes, the retained cells are recovered. Analysis of the immunomagnetically isolated cells by immunofluorescence microscopy with anti-βhCG to identify trophoblast cells will reveal 95-100% labeling of the isolated cells and no staining of the depleted cells that were removed during magnetization (Table 1). In one test performed using this methodology, approximately 500-2000 cells were recovered from each patient specimen. This approach to isolate the trophoblast cells based on their binding to antibodies that distinguish them from maternal cervical cells can also be used with other technologies. For example a microfluidic device could be constructed to sort the cells based on a magnetic or fluorescent marker conjugated to antibody.

In addition to the high purity of β-hCG expressing cells after immunomagnetic isolation, cells in the non-bound fraction were not labeled by anti-β-hCG, nor were bound cells labeled with non-immune control IgG (FIG. 1).

The method, as described above, uses the isolated cells for biochemical or genetic testing to gain information about the fetus or placenta. The isolated cells are sorted into individual or small groups of cells for testing by dispersion in a multi-well plate (such as a Terasaki multi-well plate) and sorting with a Stripper micropipetter (Origio MidAtlantic Devices, Mt. Laurel, N.J.). In a test group, groups of 50 cells are suspended in 200 µl of PBS and centrifuged onto a slide utilizing a Shandon Cytospin 3 cytocentrifuge at 1500 RPM for 5 min. These fetal cells can be used for analysis of protein expression by immunofluorescence microscopy or for molecular analysis by FISH. For example, the cells were labeled with antibodies that recognize trophoblast specific proteins or proteins that are expressed by various trophoblast subpopulations. The results indicated that the isolated cells are not from the chorionic villi, but are deeply invasive extravillous trophoblast cells (Table 2). This shows that trophoblast cells invading at the base of the placenta migrate as far as the cervix where they are collected by transcervical sampling. This can be beneficial for the further development of test protocols and increases the amount of information that can be obtained during pregnancy. A similar approach could be used clinically to screen the isolated cells for protein biomarkers of fetal disorders or maternal obstetrical disorders.

Alternatively, the cells can be sorted or identified and isolated for molecular biological analysis using methods borrowed from single cell methods used for genetic analysis of cells biopsied from preimplantation embryos generated by in vitro fertilization (IVF). Isolated trophoblast cells (up to 100) can be sorted with a Stripper micropipetter as single cells that are placed individually into thin-walled PCR tubes with 2 to 6 µl of RNase-free water and frozen at −80° C. These cells can be used for testing that probes their RNA or DNA using amplification methods such as PCR or WGA. For RNA testing, it is necessary to stabilize RNA after fixed cells are removed from the fixative solution. Therefore, the initial cell washes in PBS, incubations with HLA-G-coupled nanoparticles and manipulation of cells into aliquots are all done using PBS supplemented with 20 mM ribonucleoside-vanadyl complex (New England BioLabs, Inc.) to prevent RNA degradation. Cells should be lysed immediately for RNA purification and either stored at −80° C. in a chaotropic lysis solution or converted to cDNA before storage. It is also possible to perform protein analysis that is scaled down for single or small numbers of cells, such as ELISA or mass spectrometry. After WGA, the DNA (5-50 micrograms) can be used in microarray or deep sequencing approaches to scan for genetic mutations, identify chromosome number disorders (aneuploidies) or obtain the entire genomic sequence for personalized medicine. Genetic polymorphisms can be assessed for comparison to parental polymorphisms in order to confirm that the amplified DNA is of fetal, not parental origin, as a quality assurance control.

In another embodiment, the fetal cells can be isolated from the transcervical specimens without an initial fixation using the preservative in the kit. This enables better recovery of cells and a more accurate analysis of less stable cell constituents (e.g., metabolites, RNA) and the ability to proliferate cells to obtain increased amounts of fetal DNA or produce metaphase cells for karyotyping.

The isolation can be done by rinsing the cytobrush (used as detailed herein) in ice-cold RPMI 1640 tissue culture medium containing 10% fetal bovine serum and 50 µg/ml gentamicin or another comparable combinations of culture medium with antibiotics. The specimen can be quickly brought to the laboratory and washed three times by centrifugation and resuspension in sterile PBS at 4° C., Magnetic nanoparticles conjugated to anti-mouse IgG that have been bound with mouse anti-HLA-G were then combined with the cells and incubated at 4° C. for 1 hour. Fetal cells were recovered by incubation at 4° C. in a DynaMag-Spin magnet (Life Technologies) and removal of unbound cells. This step was repeated two more times and the bound cells were recovered in 100 µl of ice-cold PBS.

Isolated fetal cells were either cultured in standard trophoblast culture medium (Kilburn et al. 2000) or fixed for immunohistochemistry. Cultured cells formed small colonies within 2-3 days, indicating that they were proliferating. Fixed cells were labeled with antibody against the beta subunit of hCG or BCL-2, followed by fluorescent secondary antibody. All isolated cells were positively labeled with both antibodies, indicating that they were indeed trophoblast and not apoptotic.

In addition to the benefits outlined above, a benefit of the single cell approach is that it can reduce the probability of false results to nearly zero. The main source of error is in the contamination of isolated trophoblast cells with maternal cells. In general, there has not been greater than 5% contamination with maternal cells. Assays of replicate individual trophoblast cells were used for multiplex amplification of sequences from genes on the X (DMD) or Y (SRY) chromosomes to determine the gender of the corresponding fetuses. Every reaction should generate a product for X if a cell is present and PCR is working, but only male cells will generate a Y amplicon. Analysis of the PCR products by agarose gel electrophoresis should therefore produce a single band if the cell is female or two bands if male. Ten cells from each sample were analyzed and produced either all single bands (Female Fetus) or all double bands (FIG. 2). The occasional single band in a male sample is presumably a contaminating maternal cell, although we have not found this in 18 patients that were analyzed this way (Table 3). Maternal cells in female samples cannot be distinguished. The high purity of trophoblast cells is revealed in the male samples where there were no cells that produced a single band. To produce a false diagnosis, all cells would have to be maternal. In the case of a female fetus, the diagnosis would still be female, and correct. In the case of a male fetus, the presence of even one fetal cell would produce a double band to indicate that the fetus is probably not female. The test could then be repeated or the sample further investigated. The probability that all replicates would be maternal cells decreases exponentially with the number of replicates and reaches 1 in 8,000 with only three replicates, assuming the isolated cells contain 95% trophoblast cells. This level of assurance is reached with four replicates if the isolated cells contain only 90% trophoblasts. For 90% purity, the probability of a false result (P) is 0.1 for one replicate (N) and decreases ten-fold with each additional single cell replicate, where $P=10^{-N}$.

The above discussion provides a factual basis for the methods and uses described herein. The methods used with and the utility of the present invention can be shown by the following non-limiting examples.

EXAMPLES

Example 1

Materials and Methods:

Patients, age 18-40, presenting for early prenatal care with a normal intrauterine pregnancy (IUP; n=37), ectopic pregnancy (EP; n=10) or blighted ovum (BO; n=5) were enrolled for collection of transcervical specimens using a cytological brush and a ThinPrep® kit (Hologic). Cells collected in PreservCyt® fixative solution were cleared of mucus by acidification, washed by centrifugation and an aliquot was prepared on a microscope slide using a Cytospin3 centrifuge. Slides were labeled with monoclonal antibody G233 recognizing HLA-G, a MHC antigen specifically expressed by trophoblast cells. All HLA-G positive cells were identified and counted on each slide. After staining with hematoxylin, the total number of cells on each slide was determined and the ratio of HLA-G positive cells to total cells was calculated. Data were compared using one-way ANOVA, the Student-Newman-Keuls posthoc test and receiver operating characteristic (ROC) analysis.

Results:

The mean gestational ages of normal IUP, EP and BO were 9, 8 and 10 weeks, respectively. Trophoblast cells were observed in 35/37 normal IUP, 6/10 EP and 4/5 BO specimens. The frequency of HLA-G positive cells in the IUP cervical samples was approximately 1 in 2000, which was 5 to 10-fold higher (p<0.001) than the average frequency in samples from patients with EP or BO. The latter two groups were not significantly different. Significantly, ROC analysis showed that EP and BO pregnancies were distinguishable from normal pregnancies with 93% sensitivity and 95% specificity.

Conclusion:

Trophoblast cells can be reliably identified among cervical cells in the first trimester by immunohistochemical staining for HLA-G. Abnormal pregnancies are predictable based on trophoblast abundance.

Example 2

Preeclampsia (PE) and intrauterine growth restriction (IUGR) are common adverse pregnancy outcomes with no reliable means for early detection. Attempts using serum protein panels to identify patients with PE or IUGR earlier than the presenting symptoms has been inconsistent. Both disorders are linked to deficient remodeling of the uterine vasculature by extravillous trophoblast (EVT) cells. EVT residing in the endocervical canal can be captured in a non-invasive procedure similar to a PAP test and isolated free of maternal cells. Serum biomarkers of IUGR and PE are dysregulated in EVT earlier in gestation than their altered levels can be detected in serum.

Methods:

PAP specimens (N=23) were collected at 5-20 weeks of gestation using a cytobrush. Medical records were subsequently searched for diagnosis of PE or IUGR. EVT cells (500-1500) were isolated using HLA-G antibody coupled to magnetic nanoparticles. Cells (~50) were affixed to slides using a Cytospin 3 cytocentrifuge, assessed for purity with anti-β-hCG, and labeled by immunofluorescence with antibodies (R&D Systems) against galectin 13 (LGALS13, a.k.a. PP13), galectin 14 (LGALS14), placental growth factor (PGF), pregnancy-associated plasma protein A (PAPPA), alpha fetal protein (AFP), endoglin (ENG), or fms-related tyrosine kinase 1 (FLT-1). Fluorescence intensity (FI) was quantified for individual cells by image analysis. FI values of 20 cells were averaged for each patient and compared by ANOVA between normal and adverse outcome groups, using a post-hoc Tukey test.

Results:

Nine patients eventually developed PE or IUGR, while 14 had normal pregnancies. Expression of LGALS13, LGALS14, PAPPA and PGF were each decreased (p<0.05) in EVT from pregnancies that later developed PE/IUGR compared to normal pregnancies. FLT-1, ENG, and AFP were each increased (p<0.05) with PE/IUGR.

Conclusions:

A novel approach for non-invasive acquisition of EVT cells permits comparison of protein expression levels with pregnancy outcomes. These findings identified a robust panel of EVT biomarkers that could inform during the first and second trimester about patient risk for PE or IUGR.

Example 3

At 5 weeks gestation, trophoblastic cells can be non-invasively retrieved from the endocervical canal using a cytobrush. These cells can be isolated from material cells using the fetal specific marker HLA-G.

Methods:

Following isolation of trophoblast cells from pregnant patients in the first and second trimester, specimens were analyzed by immunohistochemistry for HLA-G expression. Trophoblast cells were separated from maternal cells using a column-free magnetic nanoparticle separation procedure. Purity of the trophoblast specimens was calculated by staining for β-hCG. Following whole genome amplification (WGA) of maternal and fetal cell DNA, single nucleotide polymorphism (SNP) assay and gender identification was performed by polymerase chain reaction.

Results:

Maternal and fetal cells were compared after isolation from 5 patient specimens. Average total trophoblast recovery was 700 cells, average purity was above 90%. A minimum of 10 μg of DNA was obtained after WGA using either single cells or groups of 5-100 cells. SNP assays demonstrated allelic differences between maternal and trophoblast cells in all specimens. Gender was identified and confirmed from patient records.

Conclusions:

Trophoblast cells can be retrieved and isolated from the endocervical canal with acceptable purity based on their high degree of β-hCG expression. Furthermore, fetal DNA was distinct from maternal DNA indicating its utility as a platform for non-invasive prenatal testing of the intact fetal genome.

Throughout this application, various publications, including United States patents, are referenced by author and year and patents by number. Full citations for the publications are included. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Imudia A N, Kumar S, Diamond M P, Decherney A H, Armant D R. Transcervical retrieval of fetal cells in the practice of modern medicine: a review of the current literature and future direction. Fertil. Steril. 2010; 93: 1725-1730.

Imudia A N, Suzuki Y, Kilburn B A, Yelian F D, Diamond M P, Romero R, Armant D R. Retrieval of trophoblast cells from the cervical canal for prediction of abnormal pregnancy: a pilot study. Hum. Reprod. 2009; 24: 2086-2092.

Orr J W, Jr., Barrett J M, Orr P F, Holloway R W, Holimon J L. The efficacy and safety of the cytobrush during pregnancy. Gynecol. Oncol. 1992; 44: 260-262.

Rivlin M E, Woodliff J M, Bowlin R B, Moore J L, Jr., Martin R W, Grossman J H, 3rd, Morrison J C. Comparison of cytobrush and cotton swab for Papanicolaou smears in pregnancy. J. Reprod. Med. 1993; 38: 147-150.

Paraiso M F, Brady K, Helmchen R, Roat T W. Evaluation of the endocervical Cytobrush and Cervex-Brush in pregnant women. Obstet. Gynecol. 1994; 84: 539-543.

Foster J C, Smith H L. Use of the Cytobrush for Papanicolaou smear screens in pregnant women. J. Nurse. Midwifery 1996; 41: 211-217.

Holt J, Stiltner L, Jamieson B, Fashner J. Clinical inquiries. Should a nylon brush be used for Pap smears from pregnant women? J. Fam. Pract. 2005; 54: 463-464.

O'Leary P, Breheny N, Dickinson J E, Bower C, Goldblatt J, Hewitt B, Murch A, Stock R. First-trimester combined screening for Down syndrome and other fetal anomalies. Obstet. Gynecol. 2006; 107: 869-876.

Wapner R J. Invasive prenatal diagnostic techniques. Semin. Perinatol. 2005; 29: 401-404.

Handyside A H, Kontogianni E H, Hardy K, Winston R M. Pregnancies from biopsied human preimplantation embryos sexed by Y-specific DNA amplification. Nature (London) 1990; 344: 768-770.

Munne S, Howles C M, Wells D. The role of preimplantation genetic diagnosis in diagnosing embryo aneuploidy. Curr. Opin. Obstet. Gynecol. 2009; 21: 442-449.

12. Lun F M, Tsui N B, Chan K C, Leung T Y, Lau T K, Charoenkwan P, Chow K C, Lo W Y, Wanapirak C, Sanguansermsri T, Cantor C R, Chiu R W, Lo Y M. Noninvasive prenatal diagnosis of monogenic diseases by digital size selection and relative mutation dosage on DNA in maternal plasma. Proc. Natl. Acad. Sci. U.S.A. 2008; 105: 19920-19925.

Chiu R W, Chan K C, Gao Y, Lau V Y, Zheng W, Leung T Y, Foo C H, Xie B, Tsui N B, Lun F M, Zee B C, Lau T K, Cantor C R, Lo Y M. Noninvasive prenatal diagnosis of fetal chromosomal aneuploidy by massively parallel genomic sequencing of DNA in maternal plasma. Proc. Natl. Acad. Sci. U.S.A. 2008; 105: 20458-20463.

Devaney S A, Palomaki G E, Scott J A, Bianchi D W. Noninvasive fetal sex determination using cell-free fetal DNA: a systematic review and meta-analysis. JAMA 2011; 306: 627-636.

Cioni R, Bussani C, Bucciantini S, Scarselli G. Fetal cells in a transcervical cell sample collected at 5 weeks of gestation. Journal of Maternal Fetal & Neonatal Medicine 2005; 18: 271-273.

Kilburn B A, Wang J, Duniec-Dmuchowski Z M, Leach R E, Romero R, Armant D R. Extracellular matrix composition and hypoxiz regulate the expression of HLA-G and integrins in a human trophoblast cell line. Biol. Reprod. 2000; 62:739-747.

TABLE 1

Purification of Trophoblast Cells. Trophoblast cells in 24 transcervical specimens from pregnant women were isolated with HLA-G-coupled to anti-human IgG nanoparticles. HLA-G-labeled cells counts were used to predict the number of cells expected after purification, and to estimate recovery rates. Purified cells were assessed for expression of β-hCG by immunofluorescence microscopy and the percentage of positively labeled cells is shown (n = 55 to 1500 counts per specimen).

| Patient | # Expected Trophoblasts | # Trophoblast Recovered (% Expected) | β-hCG+ % |
|---|---|---|---|
| 1 | 609 | 998 (164) | 95 |
| 2 | 1260 | 248 (20) | 99 |
| 3 | 466 | 660 (141) | 99 |
| 4 | 1108 | 345 (31) | 98.8 |
| 5 | 2467 | 832 (35) | 99.2 |
| 6 | 239 | 270 (116) | 99.6 |
| 7 | 2222 | 1462 (66) | 97.8 |
| 8 | 1009 | 818 (81) | 99.6 |
| 9 | 677 | 855 (119) | 99.6 |
| 10 | 581 | 720 (124) | 99.3 |
| 11 | 570 | 570 (100) | 99.5 |
| 12 | 1027 | 622 (61) | 100 |
| 13 | 314 | 314 (282) | 100 |
| 14 | 850 | 578 (68) | 98.9 |
| 15 | 593 | 510 (86) | 100 |
| 16 | 820 | 705 (86) | 100 |
| 17 | 842 | 623 (74) | 98 |
| 18 | 575 | 593 (103) | 100 |
| 19 | 1045 | 728 (70) | 98.9 |
| 20 | 1109 | 495 (45) | 96.4 |
| 21 | 879 | 758 (86) | 100 |
| 22 | 529 | 1463 (276) | 98.4 |
| 23 | 1095 | 1020 (93) | 100 |
| 24 | 609 | 660 (108) | 100 |
| Average | | 101 ± 13% | 99 ± 0.25% |

TABLE 2

Reactivity of Isolated Cells with an Antibody Panel to Distinguish Subtype. All cells tested were stained or unstained as indicated in the right column with antibodies against proteins listed in the left column. The middle three columns indicate the known expression patterns of the proteins in human trophoblast.

| Protein | Villous Syncytotrophoblast | Villous Cytotrophoblast | Extravillous Trophoblast | HLA-G+ Cells |
|---|---|---|---|---|
| HLA-G | − | − | + | + |
| hCG, β subunit | + | + | + | + |
| KRT7 | + | + | + | + |
| hPL | + | + | + | + |
| PSG-1 | + | − | − | − |
| α6 integrin | + | + | − | − |
| E-cadherin | + | + | −/+ | − |
| VE-cadherin | − | − | + | + |
| PECAM1 | − | − | + | + |
| α1 integrin | − | − | + | + |
| MMP9 | − | + | + | + |

TABLE 3

Summary of Fetal Sexing Results. PCR assays were conducted, as in FIG. 2 to amplify sequences on X and Y chromosomes. P, patient #. Cells giving a band (Pos. Cells)/total cells assayed is shown for X and Y chromosomes. Fetal sex was confirmed by ultrasound or at birth.

| Patient | Gestational Age Weeks | X Chromosome Pos. Cells (%) | Y Chromosome Pos. Cells (%) | Verified Gender |
|---|---|---|---|---|
| 1 | 6 | 25/30 (83.3) | 0/30 (0) | Female |
| 2 | 9.2 | 10/10 (100) | 10/10 (100) | Male |
| 3 | 14.6 | 18/20 (90) | 18/20 (90) | Male |
| 4 | 7.6 | 25/25 (100) | 0/25 (0) | Female |
| 6 | 17.6 | 10/10 (100) | 0/10 (0) | Female |
| 7 | 10 | 10/10 (100) | 10/10 (100) | Male |
| 8 | 17.5 | 10/10 (100) | 10/10 (100) | Male |
| 9 | 7.3 | 5/5 (100) | 5/5 (100) | Male |
| 10 | 11 | 10/10 (100) | 10/10 (100) | Male |
| 11 | 15.2 | 9/10 (90) | 9/10 (90) | Male |
| 13 | 7.5 | 10/10 (100) | 10/10 (100) | Male |

TABLE 3-continued

Summary of Fetal Sexing Results. PCR assays were conducted, as in FIG. 2 to amplify sequences on X and Y chromosomes. P, patient #. Cells giving a band (Pos. Cells)/total cells assayed is shown for X and Y chromosomes. Fetal sex was confirmed by ultrasound or at birth.

| Patient | Gestational Age Weeks | X Chromosome Pos. Cells (%) | Y Chromosome Pos. Cells (%) | Verified Gender |
|---|---|---|---|---|
| 14 | 12 | 10/10 (100) | 0/10 (0) | Female |
| 20 | 12.4 | 10/10 (100) | 0/10 (0) | Female |
| 21 | 12 | 9/10 (90) | 0/10 (0) | Female |
| 23 | 10 | 10/10 (100) | 0/10 (0) | Female |
| 24 | 8 | 25/28 (89.3) | 25/28 (89.3) | Male |
| 25 | 14 | 6/6 (100) | 6/6 (100) | Male |
| 26 | 12 | 24/26 (92.3) | 24/26 (92.3) | Male |

What is claimed is:

1. A method of retrieving fetal cells from an endocervical sample, comprising:
   obtaining an endocervical sample;
   placing the endocervical sample in a fixative;
   removing the mucus from the endocervical sample, thereby disassociating and fixing fetal cells and maternal cells in the endocervical sample; and
   isolating disassociated fetal cells en masse from maternal cells in the endocervical sample, wherein said isolating comprises labeling fetal cells in the sample to aid in isolating the fetal cells en masse, wherein said labeling step includes labeling the fetal cells using column-free immunomagnetic nanoparticles and recovering isolated dissociated fetal cells, wherein a majority of fetal cells present in the endocervical sample are recovered as isolated dissociated fetal cells, and wherein the isolated dissociated fetal cells are characterized by purity of 90% or greater.

2. The method according to claim 1, wherein said obtaining step comprises obtaining the endocervical sample using a method selected from the group consisting of: intrauterine lavage, aspiration of cervical mucus, and removal of surface tissue from the endocervical canal.

3. The method according to claim 1, wherein said obtaining step further comprises culturing the sample in a trophoblast culture medium.

4. The method according to claim 1, further comprising identifying cells isolated in the sample for diagnostic purposes.

5. The method according to claim 4, wherein said identifying step includes analyzing cells using a method selected from the group consisting of fluorescent in situ hybridization, polymerase chain reaction with reverse transcription, polymerase chain reaction without reverse transcription, and immunohistochemistry.

6. The method according to claim 4, further comprising analyzing the identified cells using a method selected from the group consisting of: biochemical testing and whole genome amplification followed by genomic hybridization or sequencing.

7. The method of claim 1, wherein the isolating disassociated fetal cells from maternal cells comprises:
   contacting the cells of the endocervical sample with a fetal-specific antibody;
   identifying contacted cells that have bound to the fetal-specific antibody; and
   isolating the identified cells.

8. The method according to claim 1, further comprising:
   identifying fetal cells in the isolated dissociated fetal cells;
   determining fetal cell density;
   performing a genetic analysis of the fetal cells; or
   identifying one or more biomarkers in the isolated dissociated fetal cells.

9. A method of retrieving fetal cells from an endocervical sample comprising:
   obtaining an endocervical sample;
   placing the endocervical sample in a fixative;
   removing mucus from the endocervical sample;
   immunomagnetically labeling fetal cells of the endocervical sample using column-free immunomagnetic nanoparticles;
   disassociating fetal cells from maternal cells in the endocervical sample, and
   retrieving disassociated fetal cells en masse from the sample, wherein a majority of fetal cells present in the endocervical sample are recovered as dissociated fetal cells, and wherein the dissociated fetal cells are characterized by purity of 90% or greater.

10. The method of claim 1, wherein removing the mucus from the endocervical sample comprises contacting the mucus with acetic acid.

11. A method of retrieving fetal cells from an endocervical sample consisting of:
   obtaining a fixed or an unfixed endocervical sample;
   treating the sample by acidification or treating the sample with a preservative;
   centrifuging the sample and resuspending pelleted cells, thereby washing the pelleted cells, producing a washed endocervical sample;
   immunomagnetically labeling fetal cells of the washed endocervical sample using column-free immunomagnetic nanoparticles;
   disassociating fetal cells from maternal cells in the washed endocervical sample; and
   retrieving disassociated fetal cells en masse from the washed sample, wherein a majority of fetal cells present in the endocervical sample are recovered as dissociated fetal cells, and wherein the dissociated fetal cells are characterized by purity of 90% or greater.

* * * * *